United States Patent [19]

Heller

[11] Patent Number: 5,173,802
[45] Date of Patent: Dec. 22, 1992

[54] COUNTERBALANCED SUPPORTING FRAME FOR A SURGICAL MICROSCOPE

[75] Inventor: Rudolf Heller, Zurich, Switzerland

[73] Assignee: Carl-Zeiss-Stiftung, Heidenheim/Brenz, Fed. Rep. of Germany

[21] Appl. No.: 760,685

[22] Filed: Sep. 16, 1991

[30] Foreign Application Priority Data

Sep. 19, 1990 [DE] Fed. Rep. of Germany ... 9013260[U]

[51] Int. Cl.$^5$ .................... F16L 3/00; A47G 29/00
[52] U.S. Cl. .................... 359/384; 359/391; 359/392; 359/393
[58] Field of Search ............ 359/861, 862, 384, 391, 359/392, 393, 394

[56] References Cited

U.S. PATENT DOCUMENTS

| 2,815,697 | 12/1957 | Saunders-Singer | 359/391 |
| 3,762,796 | 10/1973 | Heller | 359/384 X |
| 3,887,267 | 6/1975 | Heller | 359/384 |
| 3,891,301 | 6/1975 | Heller | 350/85 |
| 4,741,607 | 5/1988 | Heller | 359/384 |
| 4,815,832 | 3/1989 | Hagano et al. | 359/384 |
| 4,867,405 | 9/1989 | Hakamura | 359/384 X |
| 4,881,709 | 11/1989 | Hakamura | 359/384 X |

FOREIGN PATENT DOCUMENTS

| 0023004 | 1/1981 | European Pat. Off. . |
| 0202399 | 11/1986 | European Pat. Off. . |
| 2320266 | 7/1976 | Fed. Rep. of Germany . |

Primary Examiner—Eugene R. LaRoche
Assistant Examiner—D. Hyun Yoo
Attorney, Agent, or Firm—Eugene Stephens & Associates

[57] ABSTRACT

Disclosed is a spatially-adjustable supporting frame for a surgical microscope unit which can be selectively locked in any adjusted position. The frame includes a hinged parallelogram which can be pivoted about a bearing supported on a column. The hinged parallelogram carries a second structure in the form of a coupled-hinge parallelogram which, in turn, carries the surgical microscope. Two counterweights are independently adjustable along paths parallel with two adjacent sides of the hinged parallelogram to permit the continuous balancing of the weight of the surgical microscope.

1 Claim, 2 Drawing Sheets

COUNTERBALANCED SUPPORTING FRAME FOR A SURGICAL MICROSCOPE

TECHNICAL FIELD

The invention relates to a spatially-adjustable supporting frame for a surgical microscope which can be locked in any position.

BACKGROUND

Such supporting frames permit a surgeon to adjust and fix in position a surgical microscope in a predetermined spatial zone without impairing his surgical activity. Preferably, it should be possible for the surgeon to adjust such supporting frames without requiring strength which would hinder his activity. In order to attain the desired mobility of the surgical microscope while requiring only minimum exertion on the part of the surgeon, it is necessary to balance the weight of the surgical microscope by a counterweight.

In the prior art supporting frame of this type described in U.S. Pat. No. 3,891,301, the weight of the surgical microscope is balanced by a pair of exchangeable and axially adjustable weights positioned, respectively, on an intermediate support and on a lever system. Exchanging or assembling and disassembling of weights, however, are not user-friendly and therefore do not meet the requirements expected of modern surgical equipment.

The invention herein provides a supporting frame that is both readily counterbalanced and easy to use.

SUMMARY OF THE INVENTION

In the inventive structure, the intermediate supporting portion is configured as a hinged parallelogram having a first side configured as a two-armed lever that can be rotated in a bearing connected with the support column. The side of the hinged parallelogram that is opposite the lever is configured as a rod, and an axially-movable first counterweight is mounted thereon. The connecting hinge between one end of the two-armed lever and the adjacent side of the parallelogram comprises a lever system which carries a second counterweight. The hinge between the opposite end of the lever and its adjacent side of the parallelogram is connected with a further coupled-hinge parallelogram that holds the surgical microscope unit.

The advantages which can be attained with the invention herein consist in particular in that the weight of the surgical microscope can be balanced optimally by shifting the position of the continuously-adjustable counterweights, and in that such balancing is user-friendly because additional weights need not be screwed on or off.

DRAWINGS

DETAILED DESCRIPTION OF THE INVENTION

Figure 1:
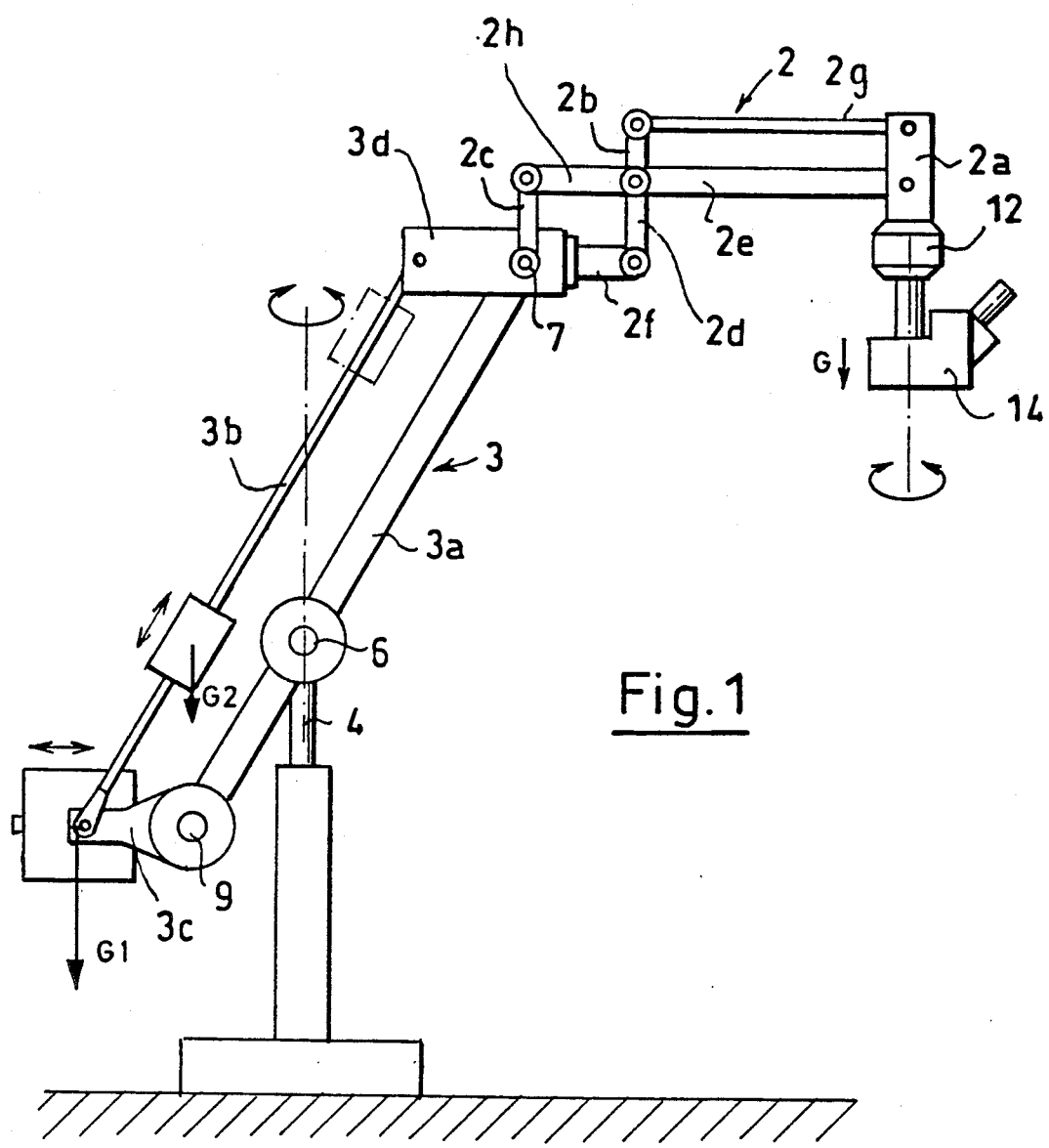
FIG. 1 is a schematic illustration of a side elevation of the inventive supporting frame.

FIG. 1 shows the height-adjustable support column 4 of a supporting frame which is connected via a pivot bearing 6 with a hinged parallelogram 3. One side of hinged parallelogram 3 is configured as a two-armed lever 3a which is rotatable in pivot bearing 6. The side opposite lever 3a is configured as a rod 3b that supports a first counterweight $G_2$ which can be shifted in an axial direction as indicated by the arrow. A hinge 9 connects one end of lever 3a with the side 3c of the hinged parallelogram, and hinge 9 carries a second counterweight $G_1$ which can be shifted in the direction of the arrow as indicated. Another hinge 7 connects the opposite end of lever 3a with an adjacent side 3d of the hinged parallelogram, and hinge 7 is also connected with the coupled-hinge parallelogram 2 (with sides 2a-2h) which supports the surgical microscope 14 in a pivot bearing 12.

Figure 2:
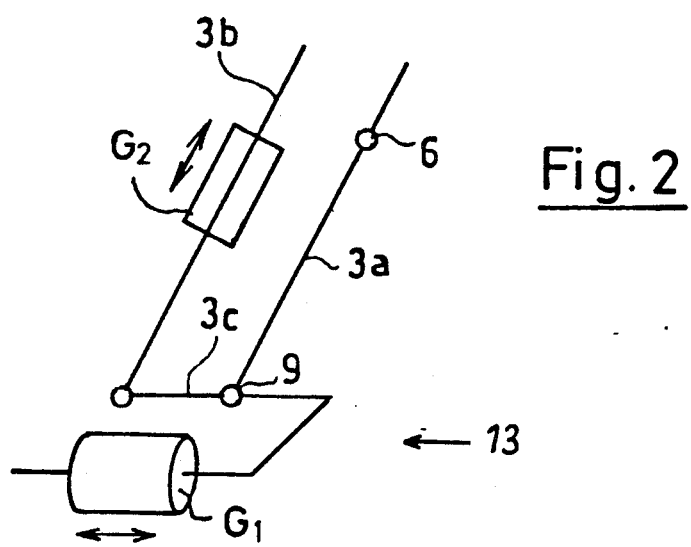
FIG. 2 is a schematic perspective illustration showing how the counterweight $G_1$ is mounted.

The cantilever system used to support counterweight $G_1$ is shown in FIG. 2 in a perspective schematic illustration and is identified by reference number 13. Weight $G_1$ can be shifted in the direction as indicated by the arrow. The sides and joints of hinged parallelogram 3 are shown schematically and have the same reference numbers as in the illustration of FIG. 1.

Figure 4:
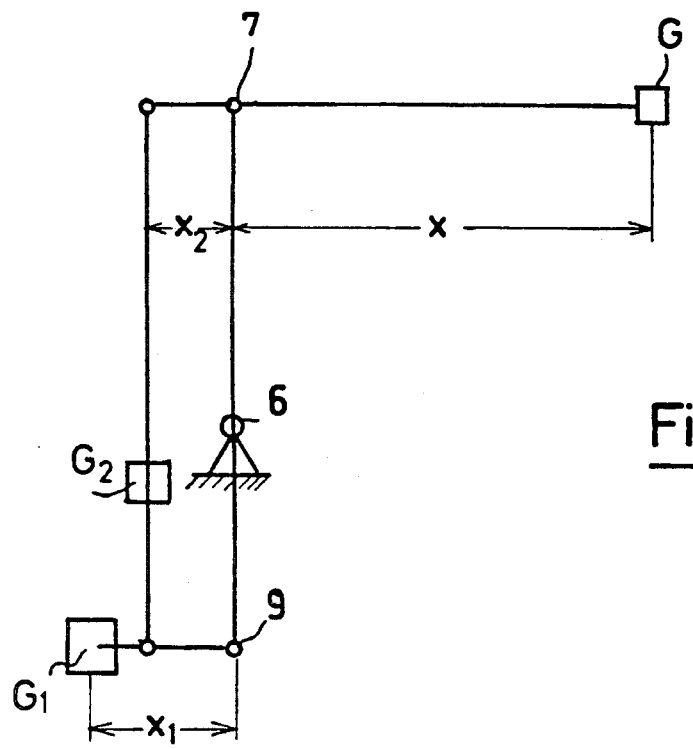
FIGS. 3 and 4 show the principle of balancing the weight of the surgical microscope.
Figure 3:
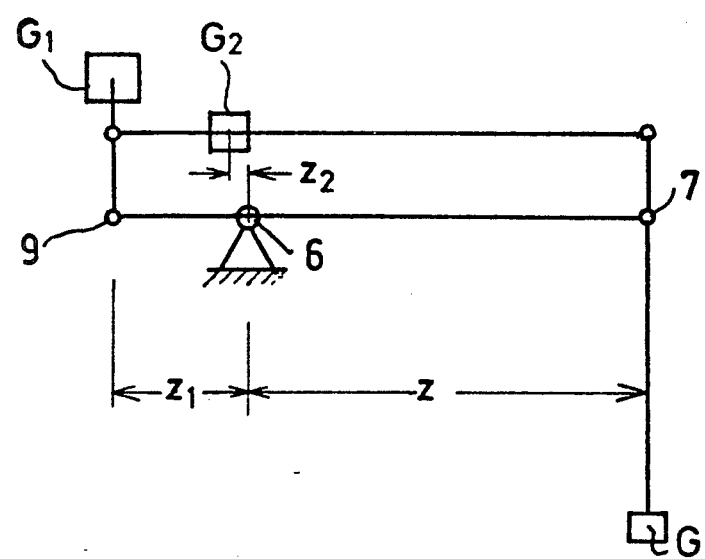

FIGS. 3 and 4 show the simple incremental balancing of the weight G (i.e., surgical microscope 14) by the positioning of counterweights $G_1$ and $G_2$ in the supporting frame. First, hinged parallelogram 3 is tilted forward, as shown in FIG. 3, i.e., it is brought into horizontal position. The balancing condition of this position is expressed by the equation:

$$G_1 \cdot Z_1 + G_2 \cdot Z_2 = G \cdot Z$$

Inasmuch as the values $G_1$, $Z_1$, $G_2$, and Z are constant, there is a formal connection between the weight of the microscope G and the length of lever arm $Z_2$ of the counterweight $G_2$. Therefore, the length of lever arm Z2 may be adjusted continuously until a first balance is achieved.

The second step shown by FIG. 4 takes place with the re-erected supporting frame. The balancing condition of this position is expressed by the following equation:

$$G_1 \cdot X_1 + G_2 \cdot X_2 = G \cdot X$$

With the exception of $X_1$ and G, the values of this equation are predetermined constants. Therefore, final balancing only requires adjustment of the length of lever arm $X_1$ of counterweight $G_1$.

The operator can then move microscope 14 as desired for observation or surgery, and the frame is locked in position. One or more of the pivot bearings of hinges 6, 7, 9, and 12 are equipped in the well-known manner with electromagnetic brakes which are released and applied selectively by the operator by means such as a hand-grip switch or a foot-pedal control (not shown).

I claim:

1. In a spatially-adjustable supporting frame for a surgical microscope unit which can be selectively locked in any adjusted position, said frame having (a) a coupled-hinge parallelogram portion for holding said microscope unit;

(b) a vertical support column; and (c) an intermediate support portion interconnecting said unit-holding portion and said support column;

the improvement wherein:

said intermediate support portion is configured as a hinged parallelogram;

a first side of the hinged parallelogram is a two-armed lever with a pivot bearing that is supported on and rotatable about said support column, said two-armed lever having connecting hinges at each end, one of said hinges interconnecting said two-armed lever and a second side of said hinged parallelogram, and the other of said hinges connecting said hinged parallelogram with said coupled-hinge parallelogram portion;

a third side opposite said first side of the hinged parallelogram is connected tat each end by respective hinges to said second side and the fourth side of said hinged parallelogram, and said third side carries a first counterweight between its said hinged ends, said first counterweight being adjustable axially along said third side; and a cantilever system associated with the hinge interconnecting said first and second ides of the hinged parallelogram carries a second counterweight that can be adjusted parallel with said second side.

* * * * *